(12) United States Patent
Spivey et al.

(10) Patent No.: US 8,540,744 B2
(45) Date of Patent: Sep. 24, 2013

(54) TISSUE PENETRATING SURGICAL DEVICE

(75) Inventors: James T. Spivey, Cincinnati, OH (US); David Stefanchik, Morrow, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 843 days.

(21) Appl. No.: 12/060,601

(22) Filed: Apr. 1, 2008

(65) Prior Publication Data

US 2009/0248055 A1  Oct. 1, 2009

(51) Int. Cl.
*A61B 17/32*  (2006.01)

(52) U.S. Cl.
USPC ........................................................ 606/180

(58) Field of Classification Search
USPC ............... 600/235; 604/164.01, 264, 506; 606/184–185, 180; 623/23.72
See application file for complete search history.

(56) References Cited

U.S. PATENT DOCUMENTS

| | | | |
|---|---|---|---|
| 982,232 A * | 1/1911 | Bartholomew | 604/1 |
| 2,767,705 A | 10/1956 | Moore | |
| 3,589,356 A | 6/1971 | Silverman | |
| 5,127,909 A * | 7/1992 | Shichman | 604/256 |
| 5,235,966 A | 8/1993 | Jamner | |
| 5,259,364 A | 11/1993 | Bob et al. | |
| 5,377,668 A * | 1/1995 | Ehmsen et al. | 600/121 |
| 5,445,644 A | 8/1995 | Pietrafitta et al. | |
| 5,450,843 A | 9/1995 | Moll et al. | |
| 5,522,795 A * | 6/1996 | Green et al. | 604/1 |
| 5,586,968 A | 12/1996 | Grundl et al. | |
| 5,624,381 A * | 4/1997 | Kieturakis | 600/206 |
| 5,658,307 A | 8/1997 | Exconde | |
| 5,836,913 A * | 11/1998 | Orth et al. | 604/107 |
| 5,885,209 A | 3/1999 | Green | |
| 5,931,845 A * | 8/1999 | Amyette | 606/162 |
| 6,007,521 A | 12/1999 | Bidwell et al. | |
| 6,030,365 A * | 2/2000 | Laufer | 604/164.01 |
| 6,371,968 B1 | 4/2002 | Kogasaka et al. | |

(Continued)

FOREIGN PATENT DOCUMENTS

| | | |
|---|---|---|
| EP | 0304380 | 2/1989 |
| EP | 1721561 | 11/2006 |

(Continued)

OTHER PUBLICATIONS

Partial European Search Report for EP 08 25 2415, mailed Oct. 24, 2008.

(Continued)

*Primary Examiner* — Ryan Severson
*Assistant Examiner* — Ashley Fishback (57) ABSTRACT

Devices and methods are provided for penetrating tissue and/or effecting movement of devices relative to tissue. In general, a surgical instrument is provided having an at least partially fabric-covered distal tip that be used to at least partially penetrate tissue by contacting the tissue with the fabric and rotating the fabric to "drill" into the tissue. The surgical instrument can be configured for delivery proximate to tissue through a working channel of a delivery device and can include an elongate shaft having in its distal portion an end effector at least partially covered in fabric. The fabric, the end effector, and/or the shaft can rotate, thereby allowing at least the fabric to penetrate the tissue and, if sufficiently rotated, causing an opening to form in the tissue. The surgical instrument and/or the delivery device can be advanced through the opening.

20 Claims, 8 Drawing Sheets

(56) References Cited

U.S. PATENT DOCUMENTS

| | | |
|---|---|---|
| 6,699,179 B2 | 3/2004 | Wendlandt |
| 6,971,990 B2 | 12/2005 | Ziegler et al. |
| 7,189,249 B2 | 3/2007 | Hart et al. |
| 2001/0044595 A1 | 11/2001 | Reydel et al. |
| 2003/0176884 A1 | 9/2003 | Berrada et al. |
| 2004/0097996 A1 | 5/2004 | Rabiner et al. |
| 2004/0143281 A1* | 7/2004 | Hart et al. ............ 606/185 |
| 2004/0199052 A1 | 10/2004 | Banik et al. |
| 2005/0171467 A1 | 8/2005 | Landman |
| 2006/0069414 A1* | 3/2006 | Imran et al. ............ 607/40 |
| 2006/0184194 A1 | 8/2006 | Pal et al. |
| 2006/0258955 A1* | 11/2006 | Hoffman et al. ............ 600/564 |
| 2007/0118167 A1 | 5/2007 | Hart et al. |
| 2008/0045803 A1 | 2/2008 | Williams et al. |
| 2008/0097474 A1* | 4/2008 | Heegaard et al. ............ 606/125 |
| 2008/0242940 A1 | 10/2008 | Stefanchik |
| 2008/0243164 A1 | 10/2008 | Stefanchik |
| 2009/0023983 A1 | 1/2009 | Stefanchik |

FOREIGN PATENT DOCUMENTS

| | | |
|---|---|---|
| EP | 1803389 | 7/2007 |
| WO | WO-0154565 | 8/2001 |
| WO | WO-0219886 | 3/2002 |
| WO | WO-03039354 | 5/2003 |

OTHER PUBLICATIONS

International Search Report for PCT/US2009/038764, mailed Jul. 15, 2009.

* cited by examiner

TISSUE PENETRATING SURGICAL DEVICE

FIELD OF THE INVENTION

The present invention relates to surgical devices useful for penetrating tissue and/or effecting movement of devices relative to tissue.

BACKGROUND OF THE INVENTION

Many surgical procedures require the movement or dissection of tissue. Space constraints as well as the relative remoteness of a distal end of a surgical tool from the surgeon can make it difficult to move tissue. In other surgical procedures, particularly in laparoscopic and endoscopic procedures, movement of the surgical device can be challenging because it is located in a relatively constrained space that is remote from the surgeon. Accordingly, there is a need for devices that conveniently and effectively enable the movement of tissue and/or the movement of surgical tools relative to tissue.

SUMMARY OF THE INVENTION

The present invention generally provides devices and methods for penetrating tissue and/or effecting movement of devices relative to tissue. In one aspect, a surgical method is provided that includes contacting a tissue with a fabric material, e.g., a mesh material, positioned over at least a portion of a distal portion of an elongate surgical instrument introduced into a body in a minimally invasive surgical procedure and rotating the fabric material to cause at least a portion of the instrument's distal portion to at least partially penetrate the tissue. In some embodiments, the method can also include advancing the surgical instrument toward the tissue through a working channel of a delivery device, e.g., an endoscope.

The tissue can include any tissue, e.g., a body lumen, an organ, etc., and in an exemplary embodiment, the tissue includes digestive tract tissue, e.g., a bowel wall, a colon wall, etc.

The elongate surgical instrument can have a variety of sizes, shapes, and configurations. For example, the distal portion of the elongate surgical instrument can be in the shape of a truncated cone, or it can be substantially cylindrical. As another example, the distal portion can taper toward its distal end. In some embodiments, the surgical instrument has a coiled shaft with a braided material over at least a portion of its outer surface.

In some embodiments, the surgical instrument can be placed adjacent to a tissue wall and the fabric material rotated to create a full thickness opening through the tissue wall. The method can also include advancing an endoscope or other device through the opening.

The fabric material can be rotated in a variety of ways, such as by manually rotating a proximal portion of the surgical instrument. The fabric material can rotate with or independent of the distal portion of the surgical instrument.

In some embodiments, the method includes allowing the tissue penetration to be viewed with a visualization device positioned within the distal portion of the surgical instrument.

In another aspect, a surgical method includes positioning a distal end of a surgical instrument adjacent to a wall of a body lumen, the distal end including a tissue engaging portion having an outer surface at least partially covered with a porous fabric, and actuating the tissue engaging portion such that at least the porous fabric rotates around an elongate axis of the tissue engaging portion to advance at least a portion of the tissue engaging portion through the wall of the body lumen. The method can have variations. For example, the method can include inserting the distal end of the surgical instrument into a body lumen prior to positioning a distal end of a surgical instrument adjacent to a wall of a body lumen. As another example, the method can include delivering at least the distal portion of the surgical instrument to a wall of a body lumen through a working channel of an endoscope.

In another aspect, a surgical method includes advancing a distal end of an elongate surgical instrument through a working channel of a delivery device, positioning the distal end of the elongate surgical instrument adjacent to a tissue, and spinning at least the distal end of the elongate surgical instrument to drill the distal end of the elongate surgical instrument at least partially into the tissue. The distal end of the elongate surgical instrument has a porous fabric positioned over at least a portion thereof, and in some embodiments, covering thereof.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods for penetrating tissue and/or effecting movement of devices relative to tissue. While the devices and methods disclosed herein can be used in conventional, open surgical procedures, they are particularly useful in minimally invasive surgical procedures, such as laparoscopic and endoscopic procedures. A person skilled in the art will also appreciate that the present invention has application in conventional open surgical and minimally invasive instrumentation as well application in robotic-assisted surgery. The principles described herein can be applicable to the particular types of tools described herein and to a variety of other surgical tools having similar functions. In addition, the tools can be used alone in a surgical procedure, or they can be used in conjunction with other devices, such as endoscopes, that facilitate minimally invasive surgical procedures.

In general, a surgical instrument is provided having an at least partially fabric-covered distal tip that be used to at least partially penetrate tissue by contacting the tissue with the fabric and rotating the fabric to "drill" into the tissue. In an exemplary embodiment, the surgical instrument can be configured for delivery proximate to tissue through a working channel of a delivery device and can include an elongate shaft having in its distal portion an end effector at least partially covered in fabric. The fabric, the end effector, and/or the shaft can rotate, thereby allowing at least the fabric to penetrate the tissue and, if sufficiently rotated, causing an opening to form in the tissue. The surgical instrument and/or the delivery device can be advanced through the opening. Because the delivery device can deliver the surgical instrument to the tissue and can thus be located proximate to the opening when it is formed by rotation of the surgical instrument, the delivery device can be advanced through the opening soon after the opening is formed, thereby helping to improve efficiency of the surgical procedure and reduce the surgical procedure's length. Using the fabric-covered distal tip to penetrate the tissue can also help reduce risk of injuring tissue on the other side of the penetrated tissue. While the tissue can include any tissue, e.g., a body lumen, an organ, etc., in an exemplary embodiment, the surgical instrument is configured for delivery through a working channel of an endoscope introduced into a bowel wall and for use in penetrating through the bowel wall.

The fabric can be formed from virtually any biocompatible material(s) having properties that enable an outer surface of the fabric to contact tissue in such a way that the fabric is able to gain a sufficient traction to enable the device to adequately grip the contacted tissue to allow the contacted tissue to be penetrated by the surgical instrument as a result of rotation of the fabric. In one embodiment, the fabric material is a porous material such as a mesh material, which can be woven or non-woven. The material from which the mesh is formed can include a variety or synthetic and non-synthetic materials. Examples of synthetic materials include polymers, such as polypropylene, polyethylene, polyester, polytetrafluoroethylene, and nylon. Examples of non-synthetic mesh materials include, but are not limited to silk, cotton, and stainless steel.

Suitable mesh materials can have a number of useful properties. One particularly useful property of the material is that it possess a high coefficient of friction such that it should be able to resist sliding relative to tissue that it contacts. That is, the movement of a low friction mesh material in contact with tissue should result in at least a portion of the end effector penetrating the tissue as a result of the fabric moving.

In one example, the mesh material can be made from a number of cords of fiber that are spaced apart from each other and connected at various points of intersection. Each cord can be formed from a plurality of fine denier filaments that are bundled together, such as by braiding, twisting, or weaving. Suitable mesh materials also tend to have a relatively high porosity as a result of having a high density of holes per square inch. For example, the mesh can have in the range of about 5 to 300 holes per square inch, or in an exemplary embodiment, in the range of about 10 to 200 holes per square inch, or in another exemplary embodiment, in the range of about 15 to 30 holes per square inch. Further, the size of the holes in the mesh can vary, but they are typically in the range of about 0.002 to 0.020 inch.

One example of a suitable mesh material is a 4 mm 100 dtex, 16 needle DYNEEMA tube available from Biomedical Structures LLC of Warwick, R.I.

The non-fabric portion of the surgical instrument can be also formed from virtually any biocompatible material(s), e.g., plastic, a polymer, stainless steel, etc. Aside from the fabric which in an exemplary embodiment is flexible, any portion of the surgical instrument can be flexible and/or rigid. The end effector can be rigid (excepting the fabric material) to allow for easier maneuverability and rotation of the fabric, while the shaft can be flexible to allow its introduction into a body through an introducer device and/or into a tortuous body lumen, e.g., the colon.

Figure 1:
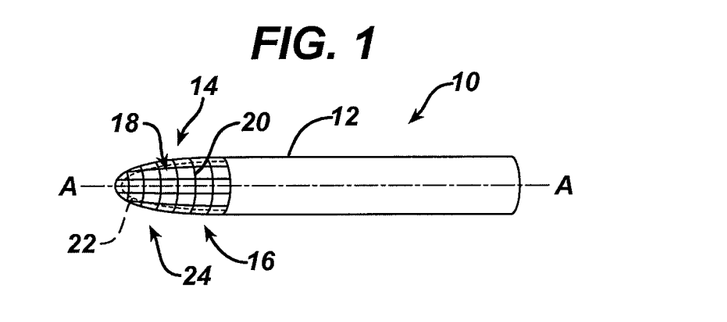
FIG. 1 is a side view of one embodiment of a tissue moving device having a conical distal end.
Figure 2:
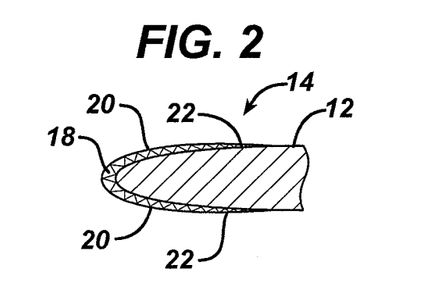
FIG. 2 is a cross-sectional view of the distal end of the tissue moving device of FIG. 1.

FIG. 1 illustrates one embodiment of a tissue moving device 10 configured to rotate and at least partially penetrate tissue. The device 10 is a generally elongate member including a shaft 12 having an end effector 14 disposed at a distal portion 16 of the shaft 12. As also shown in FIG. 2, a fabric material 18 having a tissue contacting outer surface 20 extends over at least a portion of an outer surface 22 of the shaft 12. The fabric 18 is configured to be rotatable around an elongate axis A of the end effector 14, which can also be an elongate axis of the shaft 12 such as shown in FIG. 1. The fabric 18 can rotate with the end effector 14 and/or the shaft 12, or the fabric 18 can rotate independently of the end effector 14 and/or the shaft 12, as discussed further below.

The device 10 can have a variety of sizes, shapes, and configurations able to render the device 10 suitable for a variety of surgical procedures, including open, laparoscopic and endoscopic procedures. The dimensions of the device 10, particularly its end effector 14, can vary depending upon the intended surgical technique and application. The end effector 14 and the shaft 12 can each have any length and width, either the same or different from one another, that can be constant or vary along their longitudinal lengths. However, the length and width of the end effector 14 and the shaft 12 in an exemplary embodiment are sized to allow the device 10 to be delivered to a tissue through an introducer device, e.g., through a working channel of an scoping device. Although the end effector 14 is illustrated in FIG. 1 as integrally formed with the shaft 12, the end effector 14 can be an independent element coupled in any way to a distal end of the shaft 12.

Figure 3:
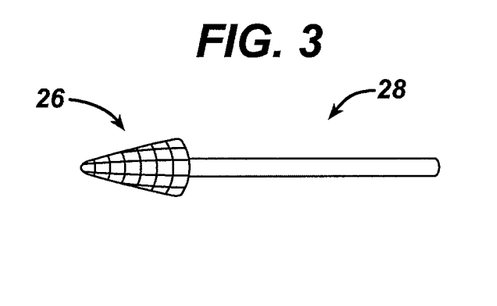
FIG. 3 is a side view of another embodiment of a tissue moving device having a conical distal end.
Figure 4:
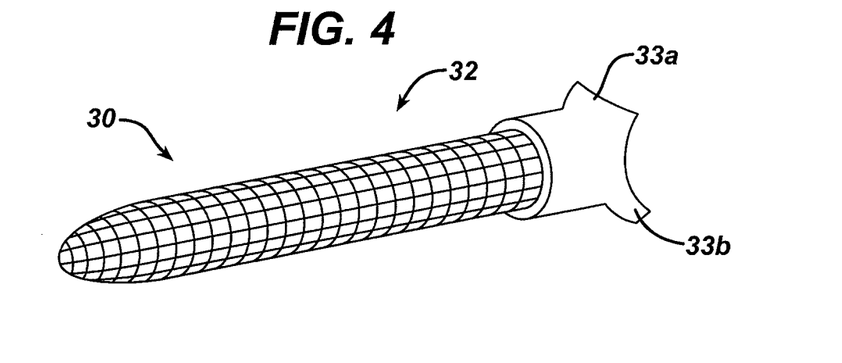
FIG. 4 is a perspective view of one embodiment of a tissue moving device having flange components.
Figure 5:
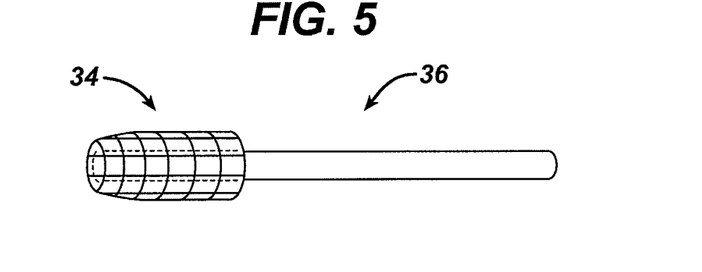
FIG. 5 is a side view of one embodiment of a tissue moving device having a distal end in the shape of a truncated cone.
Figure 6:
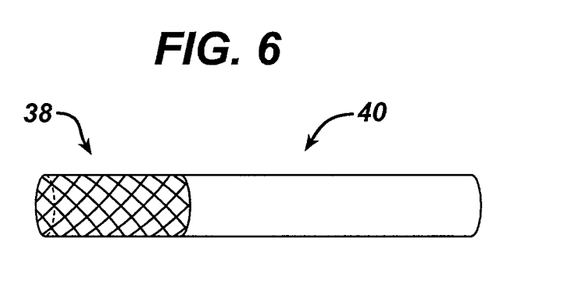
FIG. 6 is a side view of one embodiment of a tissue moving device having a cylindrical distal end.
Figure 7:
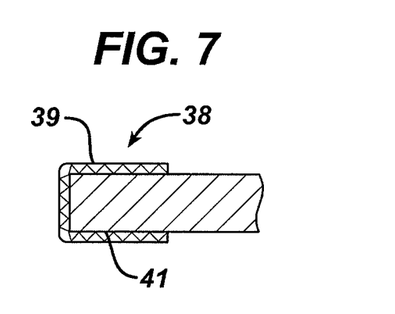
FIG. 7 is a cross-sectional view of the distal end of the tissue moving device of FIG. 6.

The end effector 14 can have a variety of shapes that make it useful to access tissue within a body. At least a distal tip 24 of the end effector 14 can have a tapered shape, such as that of a cone, e.g., the end effector 14 in FIG. 1, an end effector 26 of a device 28 in FIG. 3, and an end effector 30 in a distal portion 32 of a device in FIG. 4, or a truncated cone having a rounded or a blunted distal tip, e.g., an end effector 34 of a device 36 in FIG. 5. FIG. 4 also illustrates flange components 33a, 33b that can be slidably disposed on a shaft, making the device particularly useful in open surgery. Alternatively, the device can have a substantially cylindrical shape, e.g., an end effector 38 of a device 40 in FIG. 6 having fabric 39 covering the end effector's outer surface 41 as shown in FIG. 7. Generally, a tapered end effector can render a device able to more easily act in the manner of a wedge or a drill bit when placed and rotated at a tissue surface, a narrow opening, a tissue interface, or a junction between tissue structures.

Figure 8:
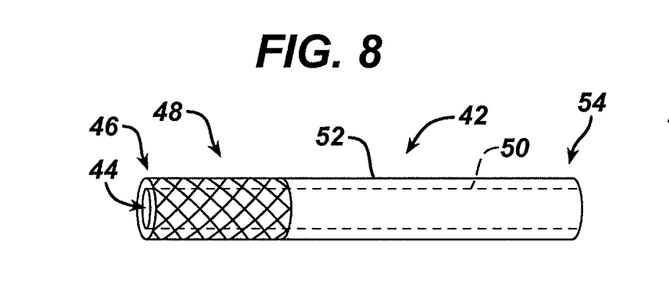
FIG. 8 is a side view of one embodiment of a tissue moving device having an open cylindrical distal end.

The fabrics on the end effectors 14, 26, 30, 34, 38 in FIGS. 1-7 cover the end effectors' distal tips such that the end effectors 14, 26, 30, 34, 38 have closed distal ends, but an end effector can have an open distal end having at least one distal opening. A device can also have one or more side openings formed in its outer surface to accommodate its fabric covering to help allow independent rotation of the fabric, as discussed further below. In an exemplary embodiment of an end effector with an open distal end shown in FIG. 8, a device 42 has an opening 44 at a distal tip 46 of its substantially cylindrical end effector 48. The opening 44 can be formed in a distal facing end of the distal tip 46 of the device 42 as shown in FIG. 8, or the opening 44 can be formed adjacent to and/or or in the vicinity of the distal facing end. If a device has a plurality of openings, the openings can have any location on the device's end effector. In any event, the opening 44 can be in communication with a lumen 50 that extends at least partially within the end effector 48 and that can extend through the device's shaft 52 to the device's proximal end 54.

Figure 9:
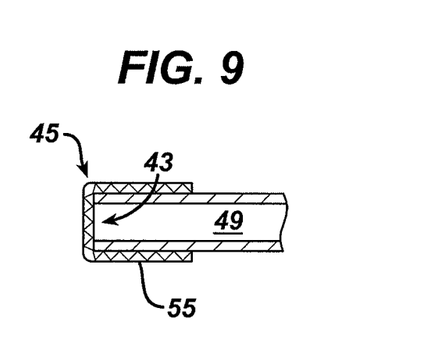
FIG. 9 is a cross-sectional view of a cylindrical distal end of a tissue moving device.

A fabric material can be mounted in a number of ways to cover at least a portion of the end effector and/or the shaft of the device. For example, as illustrated in FIG. 9, a fabric 55 can cover the device's distal end 45 and extend over the device's distal opening 43 into a lumen 49. In this way, the fabric 55 can help reduce chances of tissue, fluid, or other material dispersed by, cut by, or otherwise encountered at the device's distal end 45 from entering the shaft's lumen 49 through the lumen's distal opening 43.

Figure 10:
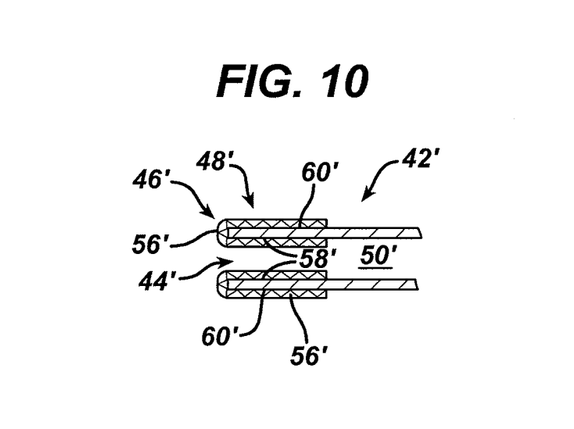
FIG. 10 is a cross-sectional view of one embodiment of the distal end of the tissue moving device of FIG. 8.

In an alternate embodiment shown in FIG. 10, a device 42' has a fabric material 56' extending around inner and outer surfaces 58', 60' of the device's end effector 48'. In this way, the fabric 56' can cover the device's distal tip 46' to allow the fabric 56' to contact tissue while keeping the device's distal opening 44' open such that material can pass through the device's inner lumen 50' via the opening 44'. For example, suction can be applied through the lumen 50' from a proximal end of the device 42' to draw material through the opening 44' and away from a surgical site, or a fluid can be introduced to a surgical site through the lumen 50', e.g., for cleansing.

Figure 11:
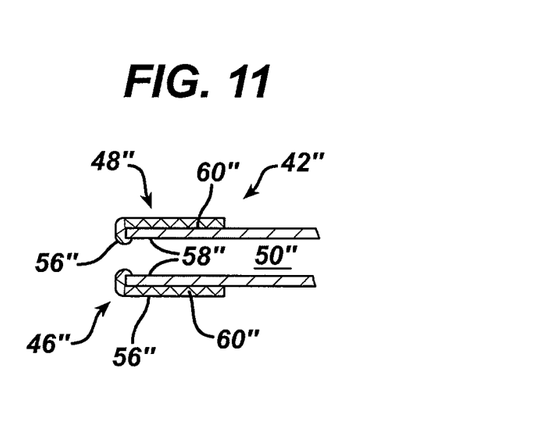
FIG. 11 is a cross-sectional view of another embodiment of the distal end of the tissue moving device of FIG. 8.

In another alternate embodiment shown in FIG. 11, a device 42" has a fabric material 56" extending around an outer surface 60" and partially around an inner surface 58" of the device's end effector 48". In this way, the device's tissue contacting distal tip 46" can be covered with the fabric 56" while keeping the device's lumen 50" substantially free of fabric to help allow interference-free passage of fluid, tools, etc. through the lumen 50".

Figure 12:
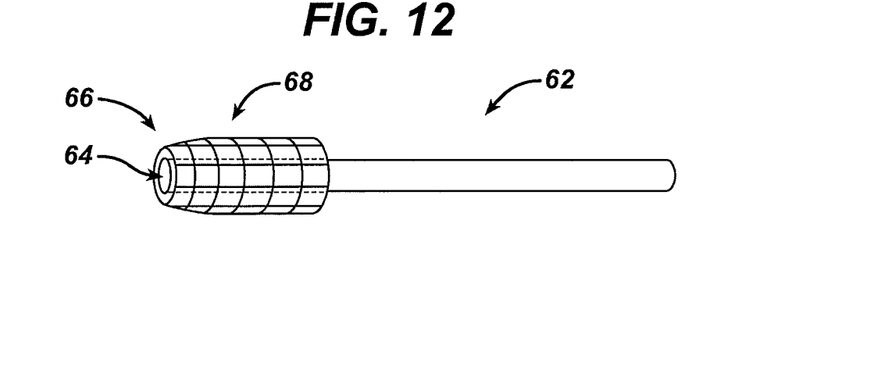
FIG. 12 is a side view of one embodiment of a tissue moving device having an open distal end in the shape of a truncated cone.

FIG. 12 illustrates another embodiment of a device 62 having an opening 64 at a distal tip 66 of a tapered-cone-shaped end effector 68.

Fabric material disposed around at least a portion of a device's end effector can be rotated in a variety of ways. For example, the entire tissue moving device can be rotated, e.g., by rotating the device from a proximal end of the device extending outside a body. The device can optionally include a handle at its proximal end to help provide a grip for manual rotation. The device can be rotated either manually or using a mechanical, electrical, and/or other automated mechanism. As another example, only the end effector of a device can be rotated in a similar manner, or only the fabric disposed around the end effector can be rotated.

Figure 13:
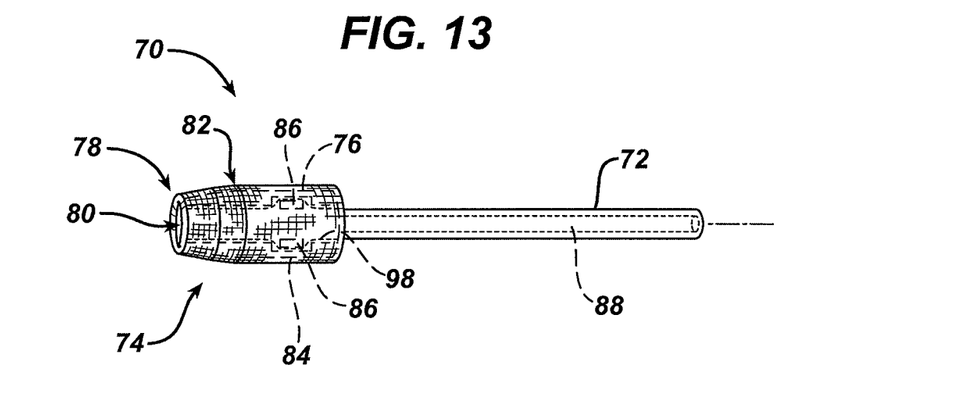
FIG. 13 is a side view of one embodiment of a tissue moving device having an actuation mechanism.

As mentioned above, fabric material can be mounted to a device to allow the fabric to be selectively movable relative to the device's shaft. In one embodiment, a tissue moving device 70 illustrated in FIG. 13 is particularly useful in minimally invasive procedures, such as for use with an endoscope. The device 70 includes an elongated shaft 72 having an end effector 74 in the form of body 76 at a distal end 78 thereof. The end effector 74 can have an opening 80 at a distal end thereof that communicates with a lumen 88 that extends through all or part of the end effector 74. A person skilled in the art will appreciate that the lumen can extend around or through the portion of the shaft 72 that is disposed within the end effector 74. However, the lumen 88 can extend within the shaft 72, and one or more side openings (not shown) can be formed in the side wall of the shaft 72 in communication with the lumen 88.

As shown in FIG. 13, a fabric material 82 can extend over at least a portion of an outer surface 84 of the end effector 74. The fabric 82 can extend over a part of the surface of the end effector 74, such as only a top surface. In an exemplary embodiment, however, the fabric 82 extends over virtually the entire outer surface 84 of the end effector 74 as illustrated. In one embodiment, the fabric 82 can be in the form of a tube that is placed within a lumen 88 and then everted, such that it extends from within the lumen 88, out of the distal opening 80 and in through side openings (not shown) in the body 76 such that the ends of the fabric 82 are joined to each other and/or to an actuator mechanism, to extend around substantially the entire outer surface 84 of the end effector 74. In this configuration, the fabric material 82 resembles a type of tread on the outer surface 84. In any event, the fabric 82 can be associated with the end effector 74 in such a way that it is able to selectively move relative to the outer surface 84 of the end effector 74. When the fabric 82 is placed in contact with tissue or an organ, movement of the fabric 82 relative to the outer surface 84 of the end effector 74 will effect relative movement of the tissue and/or the device 70. Such a configuration is described in more detail in commonly-owned, co-pending U.S. patent application Ser. No. 11/693,754 entitled "Tissue Moving Surgical Device" filed Mar. 30, 2007 and in commonly-owned, co-pending U.S. patent application Ser. No. 11/778,142 entitled "Surgical Methods And Devices With Movement Assistance" filed Jul. 16, 2007, which are hereby incorporated by reference in their entireties.

Movement of the fabric material 82 can be effected by an actuator mechanism associated with the device 210. The actuation mechanism can be of virtually any design that enables the fabric 82 to be moved selectively relative to the outer surface 84 of the body 76. In one embodiment, the actuation mechanism can be in the form of an annular ring assembly 86 attached to an outer segment of the fabric 82. A person skilled in the art will appreciate that in the form of what is essentially a tread or continuous loop, the fabric 82 will at any given state of movement have an outer segment disposed adjacent to the outer surface 84 of the body 76, which is able to engage tissue, and an inner segment, which is disposed within the lumen 88.

The ring assembly 86 can have a sliding ring component and a locking ring component. The locking ring component can be in an open position such that movement of the sliding ring component will not effect movement of the fabric 82. However, when in the locked position, the locking ring component can secure the fabric 82 to the slidable sliding ring component such that movement of the ring assembly will cause a corresponding movement of the fabric 82. The inner segment of the fabric 82 can include markings that are effective to detect motion of the fabric 82. In a neutral position, the markings are disposed within the lumen 88. When the ring assembly is moved proximally, to an actuated position, a corresponding proximal movement of the fabric 82 along the outer surface 84 of the body 76 takes place. This movement can be evidenced by the fact that markings are positioned adjacent the outer surface 84 of the body 76.

A person skilled in the art will appreciate that a variety of actuation mechanisms, other than the ring assembly, can be used. A person skilled in the art will appreciate that the actuation mechanism can be disposed internal to the device 70, as opposed to external to the device, as shown in FIG. 13. The actuation mechanism can also be an element that is separate from the device 70 rather than coupled to the device 70 as illustrated. A person skilled in the art will further appreciate that the actuator mechanism can effect movement of the fabric 82 over the outer surface 84 of the body 76 in either the proximal or the distal direction. A person skilled in the art will also appreciate that more than one actuator can be used and that such multiple actuators can work in concert with each other. For example, one actuator can effectively pull the fabric while another one can effectively push the fabric. A person skilled in the art will further appreciate that the actuation mechanism can be biased to one position, such as a forward position, such that following any proximal retraction of the actuator mechanism to effect movement of the fabric, the actuation mechanism will return to its starting position upon the release of tension from a cable. A person skilled in the art will appreciate that the return of the actuation mechanism can be effected manually and/or with the assistance of a biasing mechanism such as a spring.

As mentioned above, a separate actuator mechanism can be utilized for moving the fabric 82. For example, the actuator mechanism can be in the form of an actuator member 90 of the type illustrated in FIG. 14. As shown, the actuator member 90 is an elongate member having a proximal shaft 92 and a distal actuator structure 94 that is fabric-engaging. The actuator member 90 can be inserted within the lumen 88 to selectively contact and move the fabric 82. In one example, the actuator structure 94 can be in the form of a brush member having bristles 96 that are oriented at an acute angle with respect to the longitudinal axis A2 of actuator member 90. For example, the bristles 96 can be distally oriented or proximally oriented.

Figure 14:
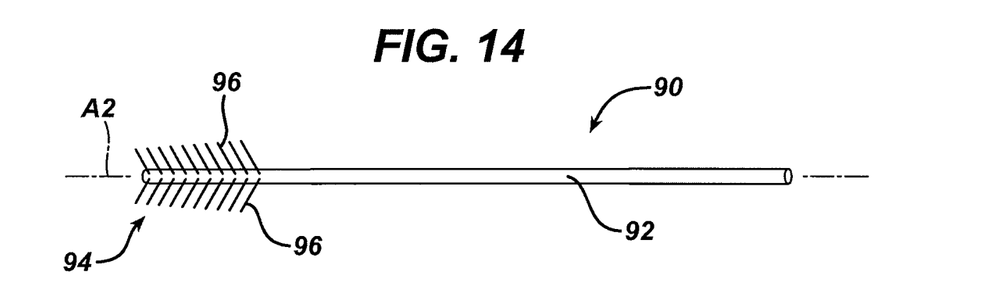
FIG. 14 is a side view of one embodiment of an actuator device useful with the tissue moving device of FIG. 13.

In one embodiment, when the bristles are distally oriented, distal movement of the actuator member 90 within the lumen 88 will enable the bristles to contact an inner segment 98 of the fabric 82 and effect proximal movement of the fabric 82 along the outer surface 84 of the device 70 by effectively pulling the fabric 82 proximally along an outer surface of the body 76, around the proximal end of body 76, and back into the lumen 88. Movement of an actuator member 90 with distally oriented bristles in a proximal direction will have no effect on the movement of the fabric 82. Alternatively, the actuator member 90 can be constructed to have proximally oriented bristles 96. With such a design distal movement of the actuator member 90 within the lumen 88 and in contact with the inner segment 98 of the fabric will have no effect on the movement of the fabric 82. However, proximal movement of the actuator member 90 while the bristles 96 are in contact with the inner segment 98 of the fabric 82 will effect distal movement of the fabric 82 along the outer surface 84 of the device 70.

Figure 15:
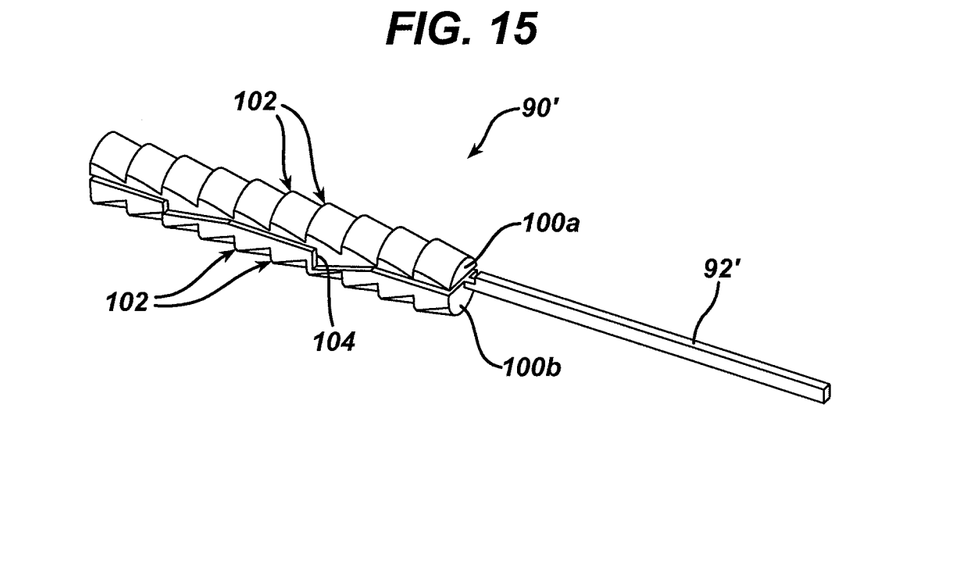
FIG. 15 is a side view of another embodiment of an actuator device useful with the tissue moving device of FIG. 13.

FIG. 15 illustrates an alternative actuator mechanism 90', which can be used in place of the bristle brush actuator 90 shown in FIG. 14. As illustrated, the actuator 90' is in the form of an elongate member 92' having at a distal end thereof two joined metal half cylinders 100a, 100b. The outer surface of each half cylinder includes teeth 102 while the surfaces where the two half cylinders join includes cam ramps 104. When one half cylinder is pushed distally relative to the other half cylinder, it ramps the other half cylinder to effectively increase the overall diameter of actuator 90' so the teeth can grip the fabric. On the return stroke the cams allow the cylinder halves to collapse the diameter of actuator 90' to ratchet across the fabric without moving the fabric to prepare for the next cycle of fabric movement.

Figure 16:
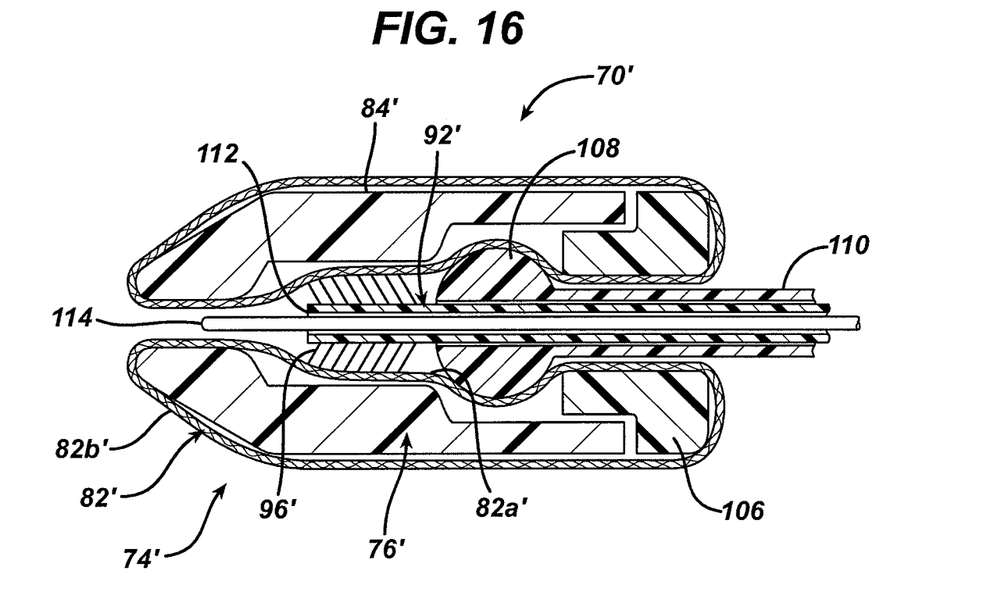
FIG. 16 is a side view of another embodiment of a tissue moving device having an actuation mechanism.

FIG. 16 illustrates a variation of the tissue moving device shown in FIG. 13. A tissue moving device 70' is likewise useful in minimally invasive procedures, such as for use with an endoscope, and it also permits visualization of tissue. The device 70' includes an end effector 74' in the form of a body 76' having a tapered distal end. As shown in FIG. 16, a fabric material 82' having inner and outer surfaces 82a', 82b' can extend over at least a portion of an outer surface 84' of the end effector 74'. In one embodiment, the fabric 82' can be everted, as described above, to extend around substantially the entire outer surface of the end effector. In any event, the fabric material 82' can be associated with the end effector 74' in such a way that it is able to selectively move relative to the outer surface 84' of the end effector 74'. Like the device described above with respect to FIG. 13, when the fabric is placed in contact with tissue, movement of the fabric relative to the outer surface of the end effector will effect relative movement of the tissue and/or the device 70'. An actuator 92' with bristles 96' of the type described above with respect to FIG. 14 can be used to selectively move the fabric relative to the outer surface 74'. A locking cap 106 can be used to lock the position of the fabric 82'. As shown in FIG. 16, the locking cap 106 cooperates with a smooth, enlarged feature 108 formed at a distal end of a shaft 110 that extends within the body 76'. In one embodiment, the shaft 110 includes a lumen formed therein through which the shaft of the actuator 92' may extend. The shaft 92' also includes a lumen 112 formed therein that is sized and configured to receive another instrument 114 such as a guidewire, a needle, and/or a miniaturized visualization device such as a camera.

This embodiment is useful in that the miniaturized visualization device can be an angioscope (e.g., having an outer diameter of about 0.035 inches) that enables a user can to view separation of tissues. This can be useful when using the device to gain access through a tissue wall so that the user knows when penetration has occurred and can safely stop the actuation of the device. The lumen 112 can also serve as a space through which to insert a guidewire (not shown), which will act as a placeholder in the opening so that other devices (e.g., dilators, balloons, cannulas) can subsequently be directed to the newly formed space after the device has been withdrawn.

Figure 17:
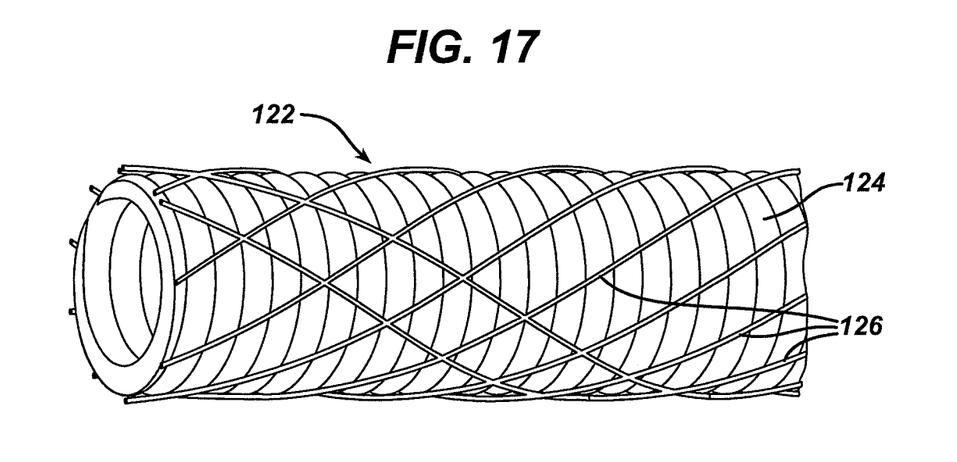
FIG. 17 is a perspective view of a distal end of one embodiment of a coil pipe shaft for a tissue moving device.
Figure 18:
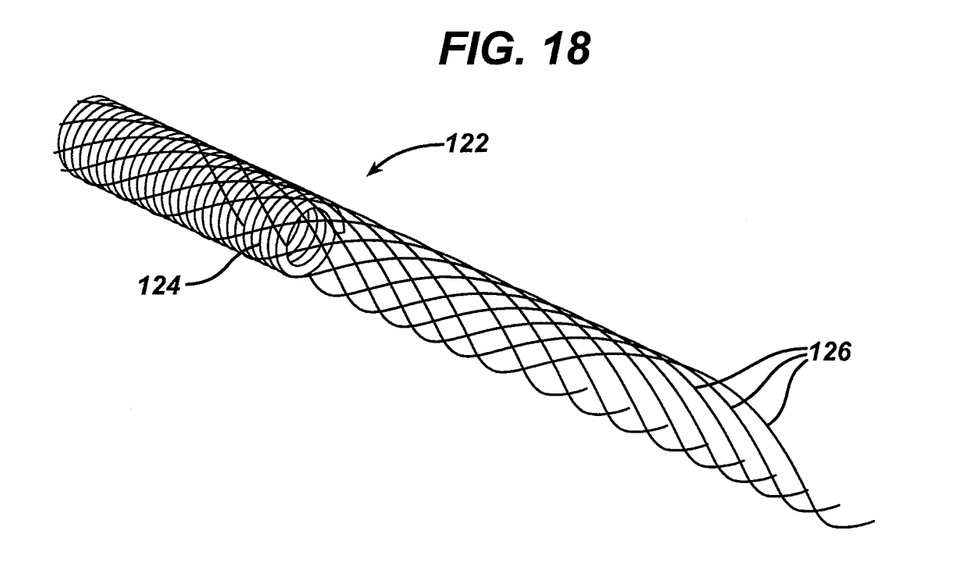
FIG. 18 is an expanded perspective view of the coil pipe of FIG. 17.

The tissue moving device's shaft can be flexible and/or rigid and can have any shape, size, and configuration. The length and width or diameter of the shaft will generally determine the type of surgery for which the device is best suited. For example, a longer and thinner shaft can be present on a device used in minimally invasive surgery while a shorter shaft can be used for a device intended for open surgery. As shown, for example, in FIG. 1, the device's shaft can have a substantially cylindrical shape and be substantially smooth (except for any openings and/or actuators coupled to the shaft). In another embodiment illustrated in FIGS. 17 and 18, a tissue moving device's shaft 122 can be flexible and include a coil pipe 124 having a tight-fitting braid 126 disposed around at least a portion of the coil pipe's outer surface in so as to constrain the coil pipe 124. The braid 126 can have any configuration, such as a criss-cross pattern formed from a plurality of individual braid cords, strings, wires, etc. The braid 126 can cover any portion of the coil pipe 124, although the braid 126 in an exemplary embodiment extends along the length of the coil pipe 124, except that a fabric-covered end effector integrated with the coil pipe 124 can exclude the braid 126. The braid 126 can help constrain the coil pipe 124 to help prevent stretching of the coil pipe 124 when it is under tension, e.g., as it is being rotated and/or moving through a working channel of a delivery device such as a scoping device. The braided coil pipe 124 can also help improve torquability of the device's shaft.

Figure 19:
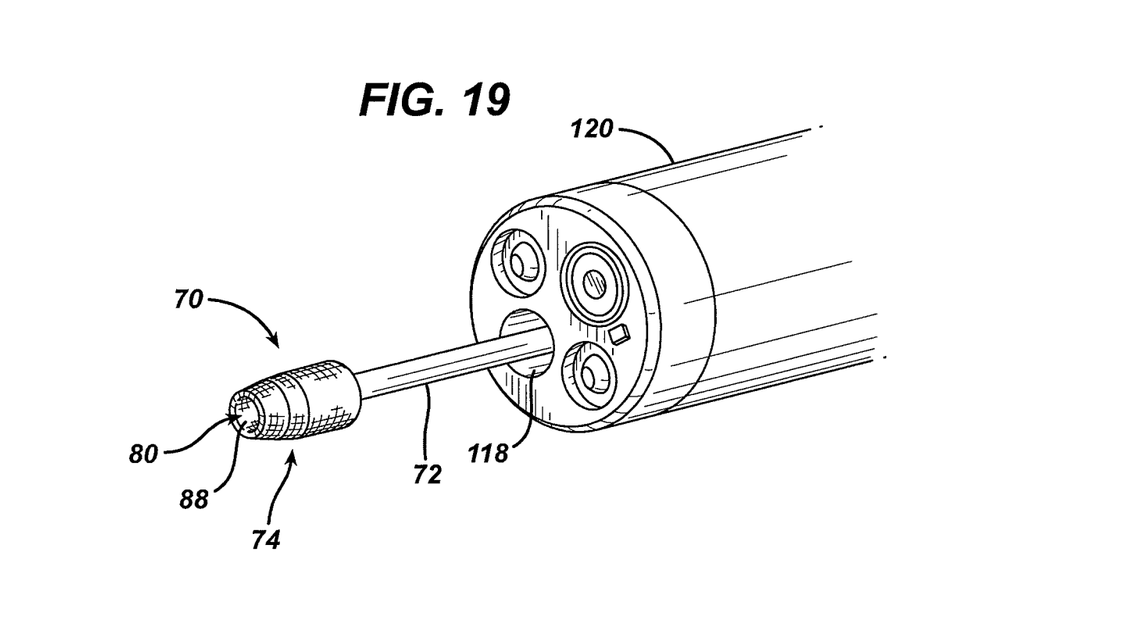
FIG. 19 is a perspective view of the tissue moving device of FIG. 13 deployed through an endoscope.

As shown in FIG. 19, the device 70 of FIG. 13 (or any other device described herein) can be used in minimally invasive surgical procedures. For example, the device 70 can be delivered to a surgical site through a working channel 118 of an endoscope 120 in a manner known to a person skilled in the art. In another example, the device 70 can be delivered through a blood vessel, such as an artery or a vein.

FIGS. 20-23 illustrate the use of a device as described herein in a surgical procedure in which it is desired to increase the size of an incision in tissue and/or to create such an opening (e.g., a full thickness opening) through which a surgical device can be passed to effect a surgical procedure. Although FIGS. 20-23 illustrate the use of a tissue moving device 130 in an endoscopic procedure involving a system that includes an endoscope 132 having a working channel 134 through which the device 130 can be delivered to a surgical site, a person skilled in the art will appreciate that this or a similar device can be used in other ways in other types of surgical procedures. Furthermore, while the affected tissue in FIGS. 20-23 can be a bowel wall 142, any tissue can be opened in a similar manner, such as the intestinal wall or the stomach wall in an endoscopic transgastric surgical procedure.

The device 130 in this embodiment includes a bullet-shaped end effector 136 having a tapered, rounded distal end 138 located at a distal end of a shaft 140. The end effector 136 has been advanced through the endoscope's working channel 134, e.g., by manipulating a proximal end (not shown) of the shaft 140 extending outside a proximal end (not shown) of the endoscope 132. As shown in an initial position in FIG. 20, the device 130 is extended beyond a distal end 144 of the endoscope 132 such that the distal end 138 of the device 130 is adjacent to a target area 146 of the tissue 142, e.g., a portion of the tissue 142 to be at least partially penetrated. Any length of the end effector 136 and/or the shaft 140 can be advanced beyond a distal end 144 of the endoscope 132 in so positioning the device's distal end 138. The end effector 136 can be positioned at any angle with respect to the target area 146 of the tissue 142, although in an exemplary embodiment a longitudinal axis A3 of the end effector 136 is substantially orthogonal to a contact surface 148 of the tissue 142 to help maximize the amount of rotational force applied to the tissue's target area 146 upon rotation of the end effector 136 and more quickly and easily penetrate the tissue 142.

Figure 20:
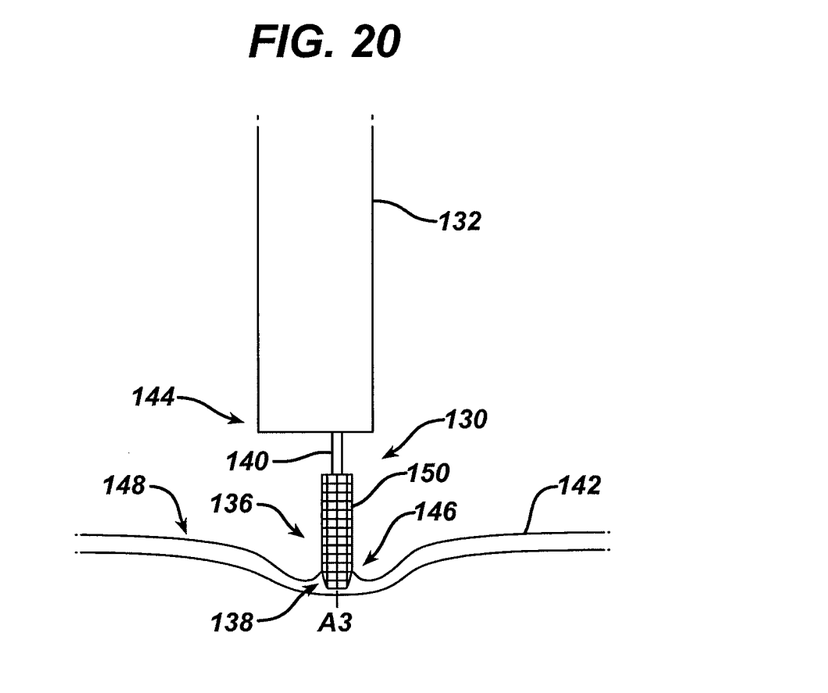
FIG. 20 is a side partially cross-sectional view of one embodiment of a tissue moving device advanced through an endoscope and positioned adjacent to tissue.

Before and/or after the device 130 has been positioned in the initial position, the target area 146 of the tissue 142 can be marked with at least one cut, score mark, visible indicator (e.g., with a dye), and/or partial opening. The device 130 can be equipped with such a marking mechanism, e.g., an integrated knife, or a separate surgical device, such as an endoscopic perforator (not shown) can be delivered to the target area 146 of the tissue 142 to mark the tissue 142 at the target area 146. The surgical device can be advanced through the endoscope 132, such as through the working channel 134 or other pathway in the endoscope 132. If the tissue moving device advanced through the endoscope 132 has an opening at its distal end, the surgical device can be advanced through the device's inner lumen when the device is disposed in the endoscope's working channel and can be advanced through the device's distal end opening to cut, score, or otherwise mark the target area 126. Alternatively or in addition, if the tissue moving device has an actuator mechanism as described above, the actuator can be in a forward position, e.g., in the vicinity of the scope's distal and 144. Upon a proximal movement of the actuator mechanism, the actuator can be retracted to proximally move a fabric material 150 on the end effector 136 likewise moves proximally with respect to an outer surface of the end effector's rigid body. This motion, in combination with the tapered shape of the end effector 136, can create or increase the size and/or depth of a cut or opening in the tissue 142. In any event, the tissue 142 at the target area 146 can be marked, and the distal end 138 of device 130 can be placed adjacent to the mark to help properly position the device 130 at the intended site and to help provide increased contact with the tissue 142, particularly if the device's distal end 138 is tapered as illustrated such that the mark can seat the distal end 138, to help improve efficiency of the device's drilling of the tissue.

Figure 21:
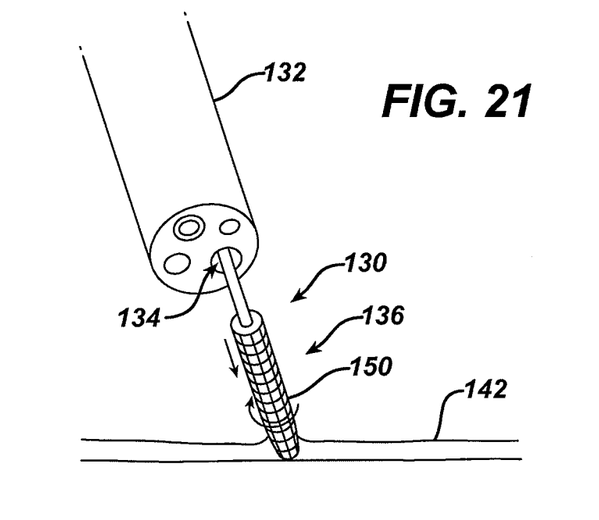
FIG. 21 is a side partially cross-sectional view of the tissue moving device of FIG. 20 being rotated.
Figure 22:
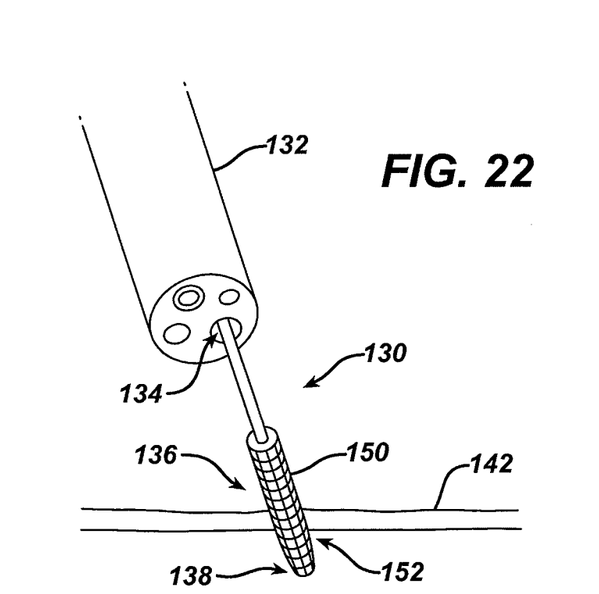
FIG. 22 is a side partially cross-sectional view of the tissue moving device of FIG. 21 penetrating through tissue.

In the initial position, at least a portion of the device's fabric 150 is in contact with a portion of the tissue 142, e.g., the contact surface 148 of the tissue 142. From the initial position the device 130 can be moved to a rotation position, illustrated in FIG. 21, where at least the fabric 150 is rotated as discussed above with respect to the tissue 142. The fabric 150 can be rotated any number of times, e.g., one complete rotation, 2.5 rotations, five complete rotations, six complete rotations, etc., and can rotate in a clockwise or a counterclockwise direction. The device's rotation, in combination with the tapered shape of the end effector 136, pushing the device 130 from its proximal end, and/or any independent movement of the fabric 150 with respect to the end effector's rigid body, can create or increase the size of the opening 152. At least a portion of the end effector 136 can penetrate a portion of the tissue 142, as shown in FIG. 21. Once the opening 152 is of sufficient size, it can allow at least a portion of the end effector 136 to move with respect to the tissue 142 such that at least a portion of the end effector 136 extends through the opening 152 and beyond the tissue 142, as shown in FIG. 22 with the device 130 in an advanced position.

Figure 23:
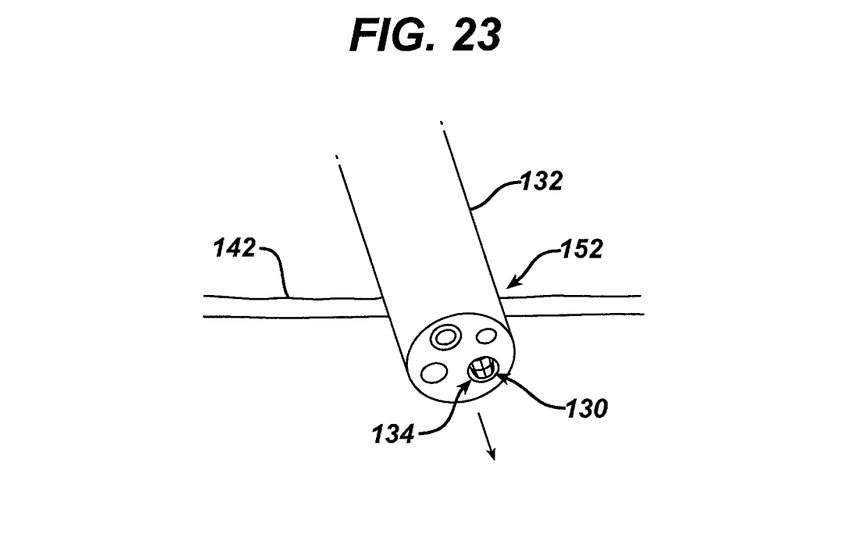
FIG. 23 is a side partially cross-sectional view of the endoscope advanced through the tissue of FIG. 22.

With the opening 152 formed, as shown in FIG. 23, the endoscope 132 and/or other surgical instruments can be advanced through the tissue opening 152 to effect a surgical procedure. Optionally, the device 130 can be proximally moved into the working channel 134 as shown, e.g., by pulling the device 130 from its proximal end. Alternatively or in addition, the opening 152 can be maintained and/or increased by the use of other devices (not shown). One or both of the device 130 and the endoscope 132 can be removed from the surgical site and the patient's body at any point following sufficient penetration of the tissue 142 and/or creation of the opening 152.

Figure 24:
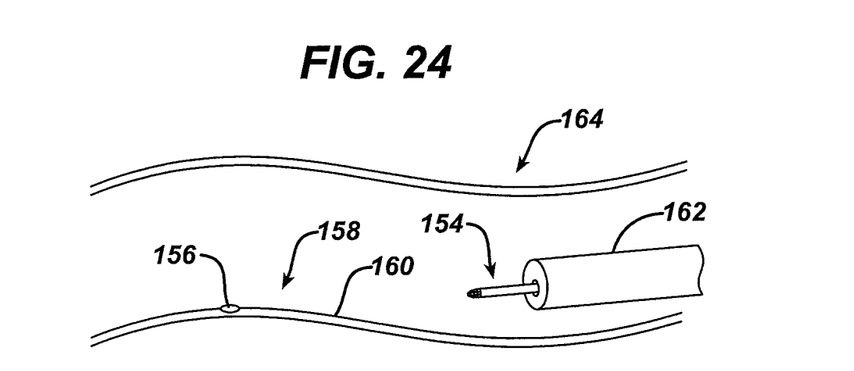
FIG. 24 is a side partially cross-sectional view of one embodiment of a tissue moving device advanced through an endoscope in a body lumen.

FIG. 24 illustrates the use of another tissue moving device 154 in another surgical procedure. FIG. 24 shows the device 154 disposed through an endoscope 162 and being advanced through a body lumen 164 (e.g., the large intestine) toward a desired location, e.g., target tissue 156 (e.g., a polyp, tissue growth, a dyed area of tissue marked for removal, etc.) on the lumen's wall 158. Once the device 154 has been placed in an initial position against a desired location on an inner surface 160 of the lumen wall 158, the device 154 can be rotated to penetrate at least partially through the lumen wall 158, and the device 154, the endoscope 162, and/or other surgical devices can be advanced through an opening created by the device 154 as discussed above.

A person skilled in the art will appreciate that the devices described herein are also amenable to use in a variety of other surgical procedures. For example, the device can be configured for delivery through the vascular system, e.g., through an artery or a vein, to treat a condition of the artery or vein or to access another site in the body where treatment is necessary. As such, the device can be used to remove plaque from an artery or to assist in the removal of plaque, or to perform or assist in the performance of a cardiac procedure. It is further understood that the methods and devices disclosed herein are applicable to use of the device in performing a surgical procedure, as well as to deliver to a surgical site a device or another agent, e.g., a drug.

The device disclosed herein can also be designed to be disposed of after a single use, or it can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
    advancing a delivery device through an orifice into a body in a minimally invasive surgical procedure;
    advancing an elongate surgical instrument through a working channel of the delivery device toward a tissue wall, the elongate surgical instrument including an elongate end effector extending along a longitudinal axis of the elongate surgical instrument and having a fabric material extending over substantially an entire length thereof;
    contacting the tissue wall with the fabric material; and
    rotating the fabric material about the longitudinal axis of the elongate surgical instrument to cause at least a portion of a distal portion of the elongate surgical instrument to at least partially penetrate the tissue wall and create a full thickness opening through the tissue wall;
    wherein the full thickness opening is not present in the tissue wall prior to rotating the fabric material to create the full thickness opening.

2. The method of claim 1, wherein manually rotating a proximal portion of the elongate surgical instrument causes rotation of the fabric material.

3. The method of claim 1, wherein the fabric material rotates with the distal portion of the elongate surgical instrument.

4. The method of claim 1, wherein the fabric material rotates independent of the distal portion of the elongate surgical instrument.

5. The method of claim 1, further comprising advancing an endoscope through the opening.

6. The method of claim 1, further comprising allowing the tissue penetration to be viewed with a visualization device positioned within the distal portion of the elongate surgical instrument.

7. The method of claim 6, wherein the visualization device is positioned within a lumen extending through the elongate surgical instrument.

8. The method of claim 7, wherein the visualization device views the tissue penetration through an opening formed in the distal tip of the elongate surgical instrument.

9. The method of claim 1, wherein the distal portion is in the shape of a truncated cone.

10. The method of claim 1, wherein the distal portion tapers toward its distal end.

11. The method of claim 1, wherein the distal portion is substantially cylindrical.

12. The method of claim 1, wherein the delivery device is an endoscope.

13. The method of claim 1, wherein the elongate surgical instrument comprises a coiled shaft having a braided material over at least a portion of an outer surface of the coiled shaft.

14. The method of claim 1, wherein the fabric material comprises a mesh material.

15. A surgical method, comprising:
    advancing a delivery device through an orifice into a body in a minimally invasive surgical procedure;
    advancing a surgical instrument through a working channel of the delivery device toward a wall of a body lumen, the surgical instrument including an elongate tissue engaging portion extending along a longitudinal axis of the surgical instrument and having a porous fabric extending over substantially an entire length thereof;
    positioning a distal end of the tissue engaging portion adjacent to the wall of the body lumen; and
    actuating the tissue engaging portion such that at least the porous fabric rotates about the longitudinal axis of the surgical instrument to advance at least a portion of the tissue engaging portion through the wall of the body lumen and create a full thickness opening through the wall of the body lumen;
    wherein the full thickness opening is not present in the wall of the body lumen prior to rotating the porous fabric to create the full thickness opening.

16. The method of claim 15, wherein the wall of the body lumen comprises the colon wall.

17. The method of claim 15, further comprising inserting the distal end of the surgical instrument into the body lumen prior to positioning the distal end of the surgical instrument adjacent to the wall of the body lumen.

18. The method of claim 15, wherein the delivery device comprises an endoscope.

19. The method of claim 15, wherein the tissue engaging portion is actuated with the distal end of the surgical instrument positioned adjacent to the wall on a first side of the wall, and wherein rotation of the fabric causes the full thickness opening to be formed in the wall to allow at least the portion of the tissue engaging portion to be advanced from the first side of the wall through the opening to a second, opposite side of the wall.

20. A surgical method, comprising:
  advancing a delivery device through an orifice into a body in a minimally invasive surgical procedure;
  advancing an elongate surgical instrument having a longitudinal axis through a working channel of the delivery device, a distal end of the elongate surgical instrument including an elongate end effector extending along the longitudinal axis of the elongate surgical instrument and having a porous fabric positioned over substantially an entire length thereof;
  positioning the end effector of the elongate surgical instrument adjacent to a tissue wall; and
  spinning at least the end effector of the elongate surgical instrument about the longitudinal axis to drill the end effector of the elongate surgical instrument at least partially into the tissue wall and create a full thickness opening in the tissue wall;
  wherein the full thickness opening is not present in the tissue wall prior to spinning at least the distal end of the elongate surgical instrument to create the full thickness opening.

* * * * *